United States Patent [19]
Pietroski et al.

[11] Patent Number: 5,456,254
[45] Date of Patent: Oct. 10, 1995

[54] FLEXIBLE STRIP ASSEMBLY HAVING INSULATING LAYER WITH CONDUCTIVE PADS EXPOSED THROUGH INSULATING LAYER AND DEVICE UTILIZING THE SAME

[76] Inventors: Susan M. Pietroski, 637 Webster St., Palo Alto, Calif. 94301; Mark S. Varner, P.O. Box 1245, Boulder Creek, Calif. 95006; Mir A. Imran, 741 Barron Ave., Palo Alto, Calif. 94306

[21] Appl. No.: 223,111

[22] Filed: Apr. 5, 1994

Related U.S. Application Data

[63] Continuation-in-part of Ser. No. 127,699, Sep. 28, 1993, which is a continuation-in-part of Ser. No. 919,198, Jul. 24, 1992, Pat. No. 5,279,299, which is a continuation-in-part of Ser. No. 656,764, Feb. 15, 1991, Pat. No. 5,156,151.

[51] Int. Cl.$^6$ .............................. A61B 5/04; A61N 1/04
[52] U.S. Cl. .......................... 128/642; 607/116; 607/122
[58] Field of Search .............................. 128/642; 607/115, 607/116, 122, 123, 125–128

[56] References Cited

U.S. PATENT DOCUMENTS

| | | | |
|---|---|---|---|
| 4,735,208 | 4/1988 | Wyler et al. | 128/642 |
| 4,837,049 | 6/1989 | Byers et al. | 128/642 X |
| 5,324,322 | 6/1994 | Grill et al. | 128/642 X |

FOREIGN PATENT DOCUMENTS

| | | | |
|---|---|---|---|
| 0269096 | 6/1989 | Germany | 607/115 |

OTHER PUBLICATIONS

Mercer et al., "Photolithographic Fabrication and Phisiological Performance of Microelectrode Arrays for Neural Stimulation" IEEE on Biomed. Eng. vol. BME–25 No. 6 Nov. '78. 607/116.

Sonn et al., "A prototype flexible microelectride array for implant–prosthesis applications", Med. & Bio. Eng. Nov. 1974. 128/642.

Primary Examiner—Lee S. Cohen
Assistant Examiner—Jeffrey R. Jastrzab
Attorney, Agent, or Firm—Flehr, Hohbach, Test, Albritton & Herbert

[57] ABSTRACT

A flexible elongate strip assembly for use in a medical device and including at least one longitudinally-extending layer of an insulating material having substantially planar spaced-apart parallel outer and inner surfaces. A plurality of pads formed from a conductive material are attached to the inner surface of the layer in longitudinally spaced-apart positions. The layer is provided with a plurality of openings extending between the outer and inner surfaces in spaced-apart positions so as to expose through the outer surface at least a portion of each pad. A plurality of spaced-apart generally parallel traces are attached to the inner surface and extend longitudinally of the layer from the pads. The exposed portion of each pad can serve as a conductive surface of an electrode.

12 Claims, 2 Drawing Sheets

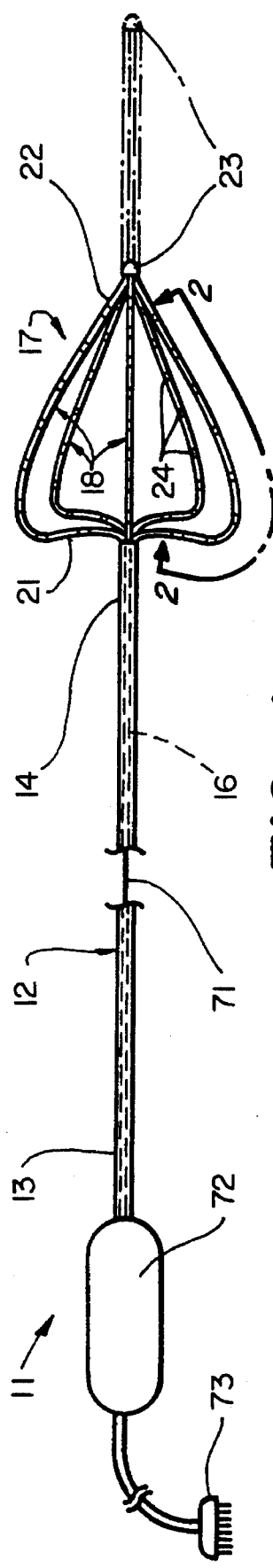
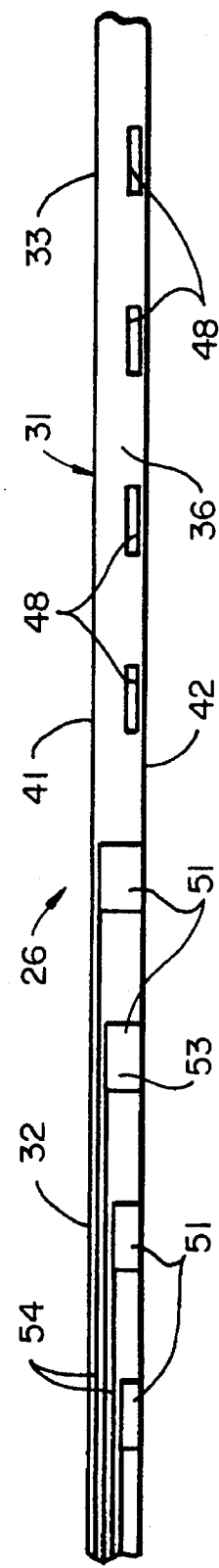
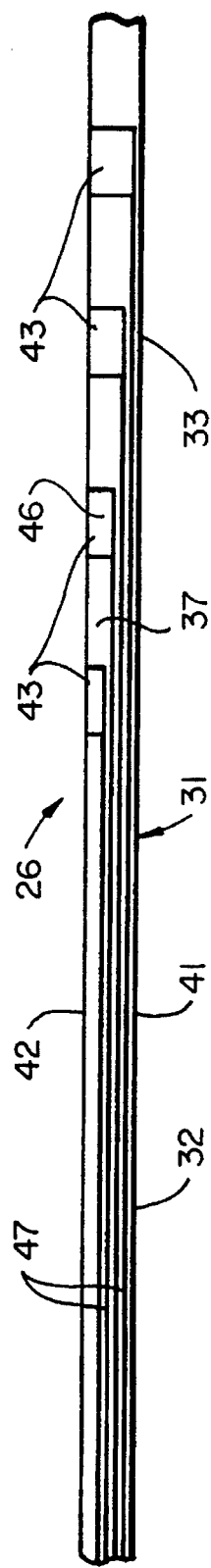

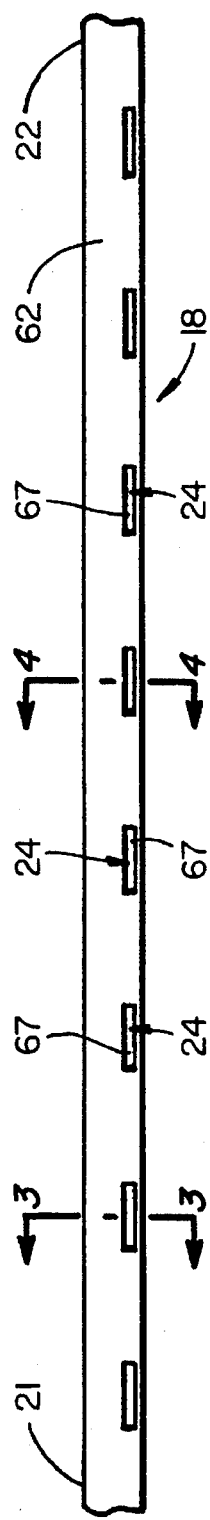
FIG_2
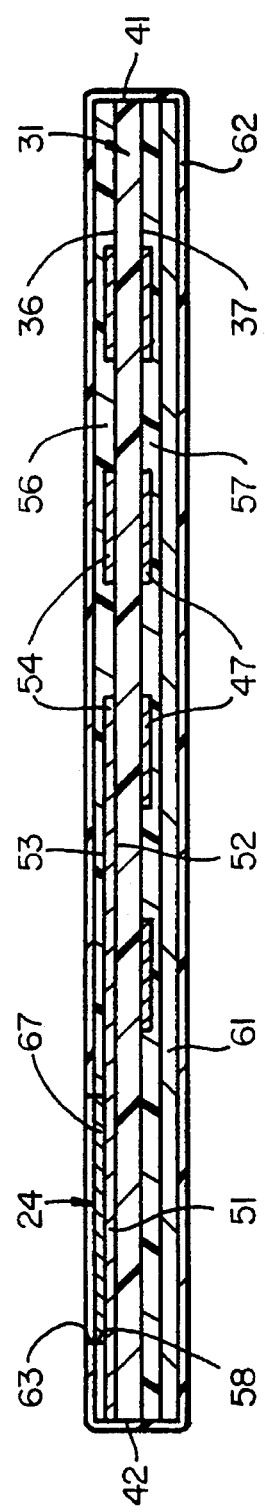
FIG_3
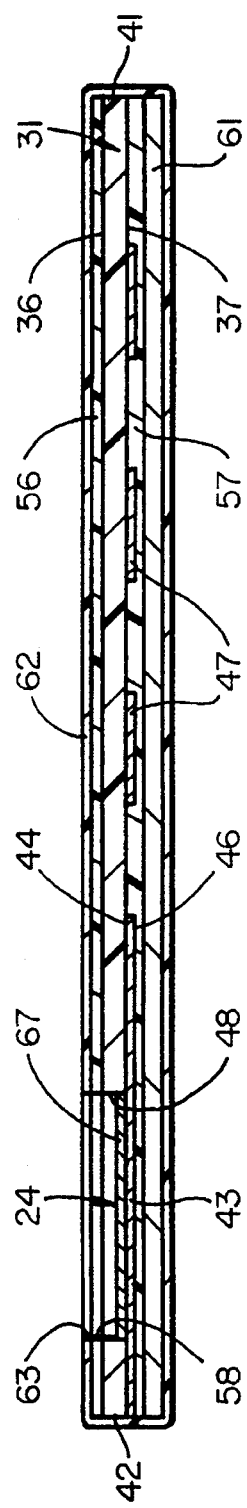
FIG_4

FLEXIBLE STRIP ASSEMBLY HAVING INSULATING LAYER WITH CONDUCTIVE PADS EXPOSED THROUGH INSULATING LAYER AND DEVICE UTILIZING THE SAME

CROSS-REFERENCE TO RELATED APPLICATIONS

This application is a continuation-in-part of application Ser. No. 08/127,699 filed Sep. 28, 1993, which is a continuation-in-part of application Ser. No. 07/919,198 filed Jul. 24, 1992, now U.S. Pat. No. 5,279,299 which is a continuation-in-part of application Ser. No. 07/656,764 filed Feb. 15, 1991, now U.S. Pat. No. 5,156,151.

BACKGROUND OF THE INVENTION

1. Field of the Invention

This invention pertains generally to flexible elongate strip assemblies and, more particularly, to flexible elongate strip assemblies for use with medical devices.

2. Description of the Related Art

It has been found that the spacial requirements of feedthrough holes or vias limit the number of traces and hence electrodes which can be carried by a layer of a multilayer strip assembly. Because of the foregoing, there is a need for a new and improved flexible elongate strip assembly which overcomes the above named disadvantages and can be used with a medical device.

Objects of the Invention

In general, it is an object of the present invention to provide a flexible elongate strip assembly which does not utilize feedthrough holes or vias.

Another object of the invention is to provide a flexible elongate strip assembly of the above character which permits an increased number of conductive traces and electrodes to be carried by a layer thereof.

Additional objects and features of the invention will appear from the following description from which the preferred embodiments are set forth in detail in conjunction with the accompanying drawings.

BRIEF DESCRIPTION OF THE DRAWINGS

FIG. 1 is a side elevational view of a flexible elongate device incorporating the flexible strip assembly of the present invention.

FIG. 2 is an enlarged side elevational view of the flexible strip assembly shown in FIG. 1 taken along the line 2—2 of FIG. 1.

FIG. 3 is a cross-sectional view of the flexible strip assembly of FIG. 2 taken along the line 3—3 of FIG. 2.

FIG. 4 is a cross-sectional view of the flexible strip assembly of FIG. 2 taken along the line 4—4 of FIG. 2.

FIG. 5 is a top plan view of a flex circuit incorporated in the flexible strip assembly of FIG. 2.

FIG. 6 is a bottom plan view of the flex circuit of FIG. 5.

SUMMARY OF THE INVENTION

In general, the flexible elongate strip assembly of the present invention is for use in a medical device and includes at least one longitudinally-extending layer of an insulating material having substantially planar spaced-apart parallel outer and inner surfaces. A plurality of pads formed from a conductive material are attached to the inner surface of the layer in longitudinally spaced-apart positions. The layer is provided with a plurality of openings extending between the outer and inner surfaces in spaced-apart positions so as to expose through the outer surface at least a portion of each pad. A plurality of spaced-apart generally parallel traces are attached to the inner surface and extend longitudinally of the layer from the pads. The exposed portion of each pad can serve as a conductive surface of an electrode.

Detailed Description

More in particular, a flexible elongate medical device of the present invention can be in the form of a catheter 11 of the type disclosed in U.S. Pat. No. 5,156,151 and copending application Ser. No. 08/044,255 filed Apr. 7, 1993 for mapping the wall of a chamber of the heart having blood therein. As disclosed therein and as illustrated in FIG. 1, endocardial mapping catheter 11 includes a flexible elongate tubular member or shaft 12 which is formed of a suitable material such as plastic and is circular in cross section. Shaft 12 has a proximal extremity 13 adapted to be disposed outside of a human body to permit access to and operation of catheter 11 and a distal extremity 14 adapted to be inserted into the body for performing an operation in the body. At least one lumen 16 extends from proximal extremity 13 to distal extremity 14 of the shaft.

A flexible means in the form of basket assembly 17 is carried by distal extremity 14 and is moveable between a first or contracted position, shown in dotted lines in FIG. 1, and a second or expanded position, shown in solid lines in FIG. 1. Basket assembly 17 is provided with a plurality of longitudinally extending flexible elongate strip assemblies or arms 18 which have an outwardly bowed shaped memory for expanding the basket assembly into engagement with the wall of the heart. Arms 18 have proximal extremities or end portions 21 which are joined to distal extremity 14 of shaft 12 and distal extremities or end portions 22 which are joined at tip 23 of basket assembly 17. When the basket assembly is expanded as illustrated in FIG. 1, arms 18 are circumferentially and symmetrically spaced-apart. A plurality of at least eight longitudinally spaced-apart electrodes 24 are supported and carried by each arm 18 for engaging the heart wall.

Each arm 18, one of which is illustrated in FIG. 2, is multilayered and includes at least one longitudinally-extending flex circuit 26, illustrated in FIGS. 5 and 6, formed from a base layer 31 of an insulating material having proximal and distal end portions 32 and 33. Elongate layer 31 is made from an insulating plastic material or substrate such as polyimide and has a length, a width ranging from approximately 0.025 to 0.050 inch and preferably approximately 0.040 inch and a thickness ranging from approximately 0.0005 to 0.0100 inch. Layer 31 further includes opposite outer and inner substantially planar spaced-apart parallel surfaces 36 and 37 extending between opposite and generally parallel first and second edges 41 and 42.

A plurality of at least three and as shown four first pads 43 having opposite planar and generally parallel surfaces 44 and 46 are disposed on inner surface 37 of distal extremity 33 and are longitudinally spaced-apart along the inner surface at approximately equal intervals in the unipolar configuration illustrated in FIG. 6. It should be appreciated, however, that layer 31 could be provided with a plurality of pad sets in a bipolar configuration and be within the scope of the present invention. In a bipolar configuration, each pad set would be longitudinally spaced-apart along the layer at approximately equal intervals and consist of two pads which are spaced apart an approximately equal distance in each pad set.

Pads 43 are made from any suitable material such as one-quarter or one-half ounce copper and preferably one-half ounce copper which is sputter deposited, rolled annealed or otherwise suitably attached or adhered at first surface 44 to inner surface 37 of layer 31. The pads are generally rectangular in shape and have a length or longitudinal dimension ranging from 0.030 to 0.100 inch and preferably approximately 0.050 inch and extend from second edge 42 toward first edge 41 to connect with a plurality of transversely spaced-apart generally parallel traces 47 extending longitudinally of inner surface 37 from proximal extremity 32 to the respective pad 43. Traces 47 are also made from copper or any other such suitable material and are formed by any suitable means such as etching away a portion of the copper or other material attached to layer 31 for pads 43. Traces 47 have a minimum width ranging from 0.0015 to 0.0035 inch. The trace nearest second edge 42 is joined to the proximalmost pad 43 and the second, third and fourth traces across inner surface 37 extend sequentially to the three other pads 43. Pads and traces 43 and 47 have a thickness ranging from approximately 0.00035 inch for one-quarter ounce copper to approximately 0.00070 inch for one-half ounce copper (see FIGS. 3 and 4).

Layer 31 is provided with a plurality of four openings 48 which are etched, laser cut or otherwise suitably formed between inner and outer surfaces 36 and 37 and are located on the layer and sized so as to expose a generally equal portion of conductive first surface 44 of each pad 43 to outer surface 36 (see FIGS. 4 and 5). More specifically, openings 48 are longitudinally spaced-apart along layer 31 so that one of the openings corresponds and aligns with each pad 43. The openings are formed near and an approximately equal distance from second edge 42. The portion of pads 43 exposed by openings 48 are generally equal in area, the exposed portion of each pad having an area ranging from 0.00012 to 0.02000 square inches. Openings 48 have a cross-sectional area not greater than the size of the smallest pad 43 and in the embodiment illustrated are generally rectangular in shape with a length ranging from 0.020 to 0.090 inch and preferably approximately 0.030 inch and a transverse dimension or width ranging from 0.005 to 0.040 inch and preferably approximately 0.008 inch.

A plurality of at least three and as shown four additional pads 51 having opposite planar and generally parallel surfaces 52 and 53 are disposed on outer surface 36 of proximal extremity 32 (see FIG. 5). Pads 51 are made from any suitable material such as copper and are attached at first surface 52 to the outer surface of layer 31 by sputter deposition or any other suitable means. The set of four pads 51 are longitudinally spaced proximal of the set of four pads 43 and pads 43 and 51 are sequentially spaced along the length of layer 31 at approximately equal intervals. The additional pads 51 extend from second edge 42 toward first edge 41 and join a plurality of transversely spaced-apart generally parallel additional traces 54 extending longitudinally from pads 51 in a proximal direction. The additional traces are adhered to outer surface 36 by any suitable means such as sputter deposition and the additional trace nearest second edge 42 extends to the proximalmost additional pad 51 and the second, third and fourth additional traces across the outer surface extend sequentially to the second, third and fourth additional pads. Additional pads and traces 51 and 54 have sizes which are generally the same as pads and traces 43 and 47.

Layer 31 is sandwiched between longitudinally-extending outer and inner layers 56 and 57 made from any suitable insulating material such as polyimide and secured to respective outer and inner surfaces 36 and 37 so as to respectively overlie and underlie layer 31. Layers or cover layers 56 and 57 serve to insulate the traces from each other and the environment and have a length and width which generally corresponds to the length and width of layer 31 and a thickness which ranges from approximately 0.0002 to 0.0020 inch. It should be appreciated that an adhesive could be disposed between layer 31 and each of layers 56 and 57 and be within the scope of the present invention.

Outer cover layer 56 is provided with a plurality of eight openings 58 which extend therethrough and are longitudinally and transversely aligned with pads 43 and 51 so as to expose at least a portion of conductive first surfaces 44 of pads 43 and conductive second surfaces 53 of additional pads 51. Openings 58 have a cross-sectional configuration or shape when viewed in plan, with corresponding area and dimensions, which generally corresponds to the shape, area and dimensions of openings 48 in layer 31. Openings 58 expose a generally similar and equal portion of pads 43 and additional pads 51.

Basket assembly 17 has an outwardly bowed-shaped memory which urges the basket assembly toward its expanded position. In this regard, arms 18 are each provided with an elongate metal strip 61 which extends beneath inner cover lay 57. Metal strip 61 is secured to flex circuit 26 and cover lays 56 and 57 by a tubular member or sheath 62 which extends around the flex circuit and cover lays and is heat-shrunk thereabout. Sheath 62 is made from any suitable material such as polyethylene terephthalate (PET) and has a thickness ranging from 0.0003 to 0.0050 inch and preferably approximately 0.0005 inch. A plurality of eight openings 63 extend through the sheath and are longitudinally and transversely aligned with openings 58 in outer cover lay 56. Openings 63 have a shape, an area and dimensions which correspond to those of openings 58.

At least a portion of first surfaces 44 of pads 43 and second surfaces 53 of additional pads 51 are exposed through arms 18 so that they can serve as conductive surfaces of electrodes 24 for mapping and/or ablating the wall of the chamber of the heart. Electrodes 24 can be augmented by plating onto copper pads 43 and 51. In this regard, a nickel flash layer (not shown) can be deposited over the exposed portions of first surfaces 44 and second surfaces 53 and a gold layer 67 having a thickness ranging from 0.00005 to 0.00020 inch can be deposited over the layer of nickel flash. A gold layer is particularly suitable as a conductive surface for an electrode in that it is inactive in blood and is also an excellent conductor.

Lead means which include wire 71 extend through lumen 16 from distal extremity 14 to proximal extremity 13 of shaft 12 and are connected to traces 47 and additional traces 54 at proximal end portions 21 of arms 18 by any suitable means such as that disclosed in copending application Serial No. 08/127,699 filed Sep. 28, 1993. A handle 72 is joined to proximal extremity 13 of shaft 12 and wire 71 and carries a connector 73 for permitting electrical connections to wire 71, traces 47 and 54 and electrodes 24.

From the foregoing, it can be seen that a new and improved flexible elongate device having a flexible elongate strip assembly which does not utilize feedthrough holes or vias has been provided. Openings 63, 58 and 48 etched through the respective sheath 62, outer cover layer 56 and base layer 31 expose at least a portion of pads 43 and 51 so that these exposed portions, after being plated with nickel and gold, can serve as electrodes. The flexible elongate strip assembly so provided permits an increased number of conductive traces and electrodes to be carried by a layer thereof.

What is claimed is:

1. A flexible elongate strip assembly for use in a medical device comprising at least one longitudinally-extending base layer of an insulating material having substantially planar spaced-apart parallel outer and inner surfaces, a plurality of generally planar first pads formed from a conductive material adherent to the outer surface of the base layer in longitudinally spaced-apart positions, each first pad being for use as a conductive surface of an electrode, a plurality of generally planar second pads formed from a conductive material adherent to the inner surface of the base layer in longitudinally spaced-apart positions, the base layer being provided with a plurality of openings extending between the outer and inner surfaces in spaced-apart positions so that at least a portion of each second pad is exposed through the outer surface for use as a conductive surface of an electrode, a plurality of spaced-apart first conductive traces connected to the first pads and adherent to the outer surface so as to be coplanar with the first pads and a plurality of spaced-apart second conductive traces connected to the second pads and adherent to the inner surface so as to be coplanar with the second pads, each trace extending longitudinally of the base layer from the respective pad.

2. A strip assembly as in claim 1 wherein the exposed portions of the second pads are generally equal in area.

3. A strip assembly as in claim 2 wherein the exposed portion of each second pad has an area ranging from 0.00012 to 0.02000 square inches.

4. A strip assembly as in claim 1 wherein the first pads form a first set of pads and wherein the second pads form a second set of pads longitudinally spaced apart from the first set of pads.

5. A strip assembly as in claim 1 together with a longitudinally-extending layer of an insulating material overlying the base layer, the longitudinally extending layer provided with a plurality of openings extending therethrough in spaced-apart positions so as to expose therethrough at least a portion of the first and second pads.

6. A strip assembly as in claim 5 wherein the exposed portions of the first and second pads are generally equal in area.

7. A flexible elongate medical device comprising a flexible elongate member having proximal and distal extremities, a plurality of spaced-apart electrodes, flexible means secured to the distal extremity of the flexible elongate member for supporting said electrodes for movement between first and second positions, the flexible means comprising a flexible elongate strip assembly which includes a base layer having a length, width and thickness in which the width is greater than the thickness, the base layer being formed of an insulating material and having substantially planar spaced-apart parallel outer and inner surfaces, at least one generally planar first pad formed from a conductive material adherent to the outer surface of the base layer for use as a conductive surface of an electrode, at least one generally planar second pad formed from a conductive material adherent to the inner surface of the base layer, the base layer being provided with at least one opening extending between the outer and inner surfaces so as to expose through the outer surface at least a portion of the second first pad for use as a conductive surface of an electrode, a first conductive trace connected to the first pad and adherent to the outer surface so as to be coplanar with the first pad and a second conductive trace connected to the second pad and adherent to the inner surface so as to be coplanar with the second pad, each trace extending longitudinally of the base layer from the respective pad.

8. A device as in claim 7 together with leads connected to the traces and extending from the distal extremity to the proximal extremity of the flexible elongate member.

9. A device as in claim 8 together with a handle coupled to the proximal extremity of the flexible elongate member and the leads.

10. A flexible elongate strip assembly for use in a medical device comprising at least one longitudinally-extending base layer of an insulating material having substantially planar spaced-apart parallel outer and inner surfaces, at least one first pad formed from a conductive material adherent to the outer surface of the base layer and at least one second pad formed from a conductive material adherent to the inner surface of the base layer, the base layer being provided with at least one opening extending between the outer and inner surfaces so as to expose through the outer surface at least a portion of the second pad, a first conductive trace adherent to the outer surface and connected to the first pad and a second conductive trace adherent to the inner surface and connected to the second pad, each first and second trace extending longitudinally of the base layer from the respective pad whereby the first pad and the exposed portion of the second pad each serve as a conductive electrode surface.

11. A strip assembly as in claim 10 wherein the first and second pads are generally coplanar with the base layer.

12. A strip assembly as in claim 11 wherein the first pad and first trace are generally coplanar and the second pad and second trace are generally coplanar.

* * * * *

UNITED STATES PATENT AND TRADEMARK OFFICE
CERTIFICATE OF CORRECTION

PATENT NO. : 5,456,254
DATED : October 10, 1995
INVENTOR(S) : SUSAN M. PIETROSKI; MARK S. VARNER; MIR A. IMRAN It is certified that error appears in the above-indentified patent and that said Letters Patent is hereby corrected as shown below:

On the title page insert the following:

-- Assignee: [73] Cardiac Pathways Corporation, Sunnyvale, Calif. --

Signed and Sealed this

Fifth Day of March, 1996

Attest:

BRUCE LEHMAN

*Attesting Officer*    *Commissioner of Patents and Trademarks*